United States Patent
Peterson et al.

(10) Patent No.: US 6,884,640 B2
(45) Date of Patent: Apr. 26, 2005

(54) METHOD AND APPARATUS FOR DETERMINING LAYER THICKNESS AND COMPOSITION USING ELLIPSOMETRIC EVALUATION

(75) Inventors: Jeffrey J. Peterson, Austin, TX (US); Charles E. Hunt, Davis, CA (US); Peter J. Bjeletich, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/437,878

(22) Filed: May 13, 2003

(65) Prior Publication Data

US 2004/0014250 A1 Jan. 22, 2004

Related U.S. Application Data

(60) Provisional application No. 60/380,599, filed on May 15, 2002.

(51) Int. Cl.[7] .................................. H01L 21/66
(52) U.S. Cl. ..................... 438/14; 438/12; 438/16; 438/17; 438/18
(58) Field of Search ..................... 438/12, 14, 16, 438/17, 18

(56) References Cited

U.S. PATENT DOCUMENTS

| | | | |
|---|---|---|---|
| 4,854,710 A | 8/1989 | Opsal et al. ............... 356/432 |
| 5,943,122 A | 8/1999 | Holmes ...................... 356/73 |
| 6,049,220 A | * 4/2000 | Borden et al. .............. 324/765 |
| 6,134,012 A | 10/2000 | Aspnes et al. .............. 356/369 |
| 6,208,418 B1 | 3/2001 | Maris ........................ 356/388 |
| 6,277,657 B1 | 8/2001 | Nozawa et al. ................ 438/8 |
| 6,330,464 B1 | * 12/2001 | Colvin et al. .............. 600/316 |
| 2004/0014250 A1 | 1/2004 | Peterson et al. ............. 438/14 |

OTHER PUBLICATIONS

Publication entitled "A Users Guide to Ellipsometry", by Harland G. Tompkins, Academic Press, Inc., 1993, Preface and pp. 33–50, and pp. 214–216.

Publication entitled "Optical Metrology", Society of Photo–Optical Instrumentation Engineers, Proceedings of a conference held Jul. 18–19, 1999.

(Continued)

Primary Examiner—Michael Tran
Assistant Examiner—Renee R. Berry
(74) Attorney, Agent, or Firm—Park, Vaughan & Fleming LLP

(57) ABSTRACT

One embodiment of the present invention provides a system that determines the composition of a layer within an integrated device. The system operates by first receiving the integrated device. Next, the system measures properties of the layer using electromagnetic radiation. The properties of the layer measured are used to determine an index of refraction for the layer. The system then solves for the composition of the layer using the index of refraction.

14 Claims, 3 Drawing Sheets

OTHER PUBLICATIONS

Publication entitled "Ellipsometry for Rapid Characterization of SI1–xGEx Layers", by M. Racanelli et al., American Institute of Physics, May 4, 1992, pp. 2225–2227.

Publication entitled "Dielectric Response of Strained and Relaxed SI1–x–yGExCy Alloys Grown by Molecular Beam Epitaxy on SI(001)", by Rudiger Lange et al., American Institute of Physics, Oct. 15, 1996, pp. 4578–4586.

Publication entitled " Optical Constants and Ellipsometric Thickness Determination of Strained SI1–xGEx:C Layers on SI (100) and Related Heterostructures", by Stefan Zollner et al., American Institute of Physics, Journal of Applied Physics, vol. 88, No. 7, pp. 4102–4108.

Publication entitled "Refined Model for Spectroscopic Ellipsometry Analysis of SIxGE1–x/SI Strained Heterostructures", by F. Ferrieu et al., American Institute of Technology, Applied Physics Letters, vol. 76, No. 15, pp. 2023–2025.

Publication entitled "Variable Angle of Incidence Spectroscopic Ellipsometry: Application to GaAs–AlxGA1–xAS Multiple Heterostructures", by Paul G. Snyder et al., American Institute of Physics, Journal of Applied Physics, Nov. 1, 1986, pp. 3293–3302.

Publication entitled "Real–Time Spectroscopic Ellipsometry Monitoring of SI1–xGEx/SI Epitaxial", by C. Pickering et al., J. Va. Sci. Technol. A 13(3), May/Jun. 1995, pp. 740–744.

* cited by examiner

METHOD AND APPARATUS FOR DETERMINING LAYER THICKNESS AND COMPOSITION USING ELLIPSOMETRIC EVALUATION

RELATED APPLICATION

This application hereby claims priority under 35 U.S.C. §119 to U.S. Provisional Patent Application No. 60/380,599, filed on 15 May 2002, entitled "Method of Determining SiGe and SiGeC Thickness and Composition Using Ellipsometric Evaluation," by inventors Jeffrey J. Peterson, Charles E. Hunt, and Peter J. Bjeletich.

GOVERNMENT LICENSE RIGHTS

This invention was made with United States Government support under Grant Nos. N00014-93-C-0114 and N00014-96-C-0219 awarded by the Office of Naval Research. The United States Government has certain rights in the invention.

BACKGROUND

1. Field of the Invention

The present invention relates to the process of fabricating integrated devices. More specifically, the present invention relates to a method and an apparatus that uses ellipsometric evaluation to determine layer thickness and composition of an integrated device.

2. Related Art

It is common practice in semiconductor factories to monitor layer thickness and composition of the various layers during fabrication of integrated devices such as integrated circuits, discrete electronic devices, Micro ElectroMechanical Systems (MEMS), optical components, materials using silicon-germanium (SiGe) and silicon-germanium-carbon (SiGeC), and other materials and devices. This monitoring is required to ensure that the integrated device will accurately perform its designed function.

Current methods of monitoring process steps during device fabrication include Rutherford back-scattering (RBS) and secondary ion mass spectrometry (SIMS). While these methods adequately measure the thickness and composition of the layer being examined, they both have drawbacks, which render them impractical for use in a production environment.

RBS can take several days to complete and can cost $50.00–$100.00 per sample. This cost is prohibitive. However, the delay of several days can be more significant. During the several day delay while the test is being completed, the production process may produce several million dollars worth of product. If the thickness and composition of a layer are not correct, all of this product may be defective. SIMS may take as long and costs even more per sample and therefore further aggravates the situation.

Hence, what is needed is a method and an apparatus for determining layer thickness and composition that is both economical and provides feedback in a commercially reasonable amount of time.

SUMMARY

One embodiment of the present invention provides a system that determines the composition of a layer during manufacture of an integrated device. The system operates by first receiving the integrated device. Next, the system measures properties of the layer using electromagnetic radiation (e.g. using ellipsometry). The properties of the layer measured during ellipsometry are used to determine an index of refraction for the layer. The system then solves for the composition of the layer using the index of refraction.

In a variation of this embodiment, the properties measured using ellipsometry include properties of returned radiation received during ellipsometry including signal amplitude, signal phase, and signal polarization.

In a further variation, modeling the properties of the layer includes accounting for an overlaying oxide layer on the integrated device.

In a further variation, solving for the composition of the layer provides the Ge composition in a SiGe layer.

One embodiment of the present invention provides a system that determines the thickness of a layer within an integrated device. The system operates by first receiving the integrated device. Next, the system measures properties of the layer using ellipsometry or other means. The properties of the layer measured during ellipsometry are modeled to determine an index of refraction for the layer. Next, the system solves for the thickness of the layer using the index of refraction.

In a variation of this embodiment, solving for the thickness of the layer produces the thickness of a SiGe layer.

One embodiment of the present invention provides a system that determines the composition of a layer within an integrated device. The system operates by first receiving the integrated device. Next, the system measures a first set of properties and a second set of properties of the layer using electromagnetic radiation, wherein the first set of properties and the second set of properties are measured for different types, wavelengths, or angles of radiation. The system then models the first set of properties of the layer to determine a first index of refraction for the layer and models the second set of properties of the layer to determine a second index of refraction for the layer. Next, the first index of refraction and the second index of refraction are applied to index of refraction models to determine the layer properties. The system repeats the steps of modeling the first set of properties, modeling the second set of properties, and applying the first index of refraction and the second index of refraction to an index of refraction model until the results of applying the first index of refraction and the second index of refraction to the index of refraction models agree. The system solves for the composition of the layer using the index of refraction.

One embodiment of the present invention provides a system that determines the thickness of a layer within an integrated device. The system operates by first receiving the integrated device. Next, the system measures a first set of properties and a second set of properties of the layer using electromagnetic radiation, wherein the first set of properties and the second set of properties are measured for different types, wavelengths, or angles of radiation. The system then models the first set of properties of the layer to determine a first index of refraction for the layer and models the second set of properties of the layer to determine a second index of refraction for the layer. The system applies the first index of refraction and the second index of refraction to index of refraction models to determine the composition of the layer. The system repeats the steps of modeling the first set of properties, modeling the second set of properties, and applying the first index of refraction and the second index of refraction to an index of refraction model until the results of applying the first index of refraction and the second index of refraction to the index of refraction models agree. The system solves for the thickness of the layer using the index of refraction.

In a variation of this embodiment, solving for the thickness of the layer produces the thickness of a SiGeC layer.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

The data structures and code described in this detailed description are typically stored on a computer readable storage medium, which may be any device or medium that can store code and/or data for use by a computer system. This includes, but is not limited to, magnetic and optical storage devices such as disk drives, magnetic tape, CDs (compact discs) and DVDs (digital versatile discs or digital video discs), and computer instruction signals embodied in a transmission medium (with or without a carrier wave upon which the signals are modulated). For example, the transmission medium may include a communications network, such as the Internet.

Performing Ellipsometry

Figure 1:
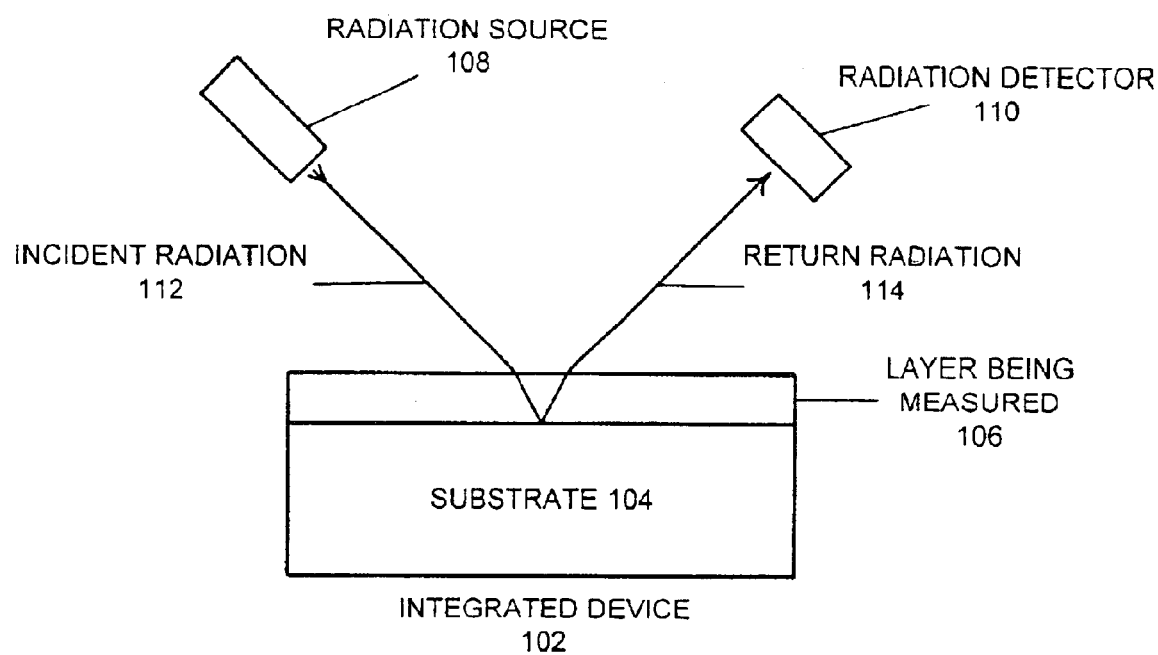
FIG. 1 illustrates an integrated device being tested in accordance with an embodiment of the present invention.

FIG. 1 illustrates an integrated device 102 being tested in accordance with an embodiment of the present invention. Integrated device 102 includes substrate 104 and layer being measured 106. Note that the layer being measured 106 can be substrate 104. Also note that there may be an oxide layer (not shown) over layer being measured 106. The system can compensate for this presence of an oxide layer.

The measurement apparatus includes radiation source 108 and radiation detector 110. Radiation source 108 provides incident radiation 112 to all or a portion of layer being measured 106. Return radiation 114 includes amplitude shifts, phase shifts, and polarization shifts relative to incident radiation 112. These amplitude shifts, phase shifts, and polarization shifts are the result of refraction within layer being measured 106 and are dependent upon the thickness and composition of layer being measured 106.

The measured amplitude shifts, phase shifts, and polarization shifts are used to determine an index of refraction for layer being measured 106. This index of refraction is applied to an index of refraction model to determine the thickness and composition of layer being measured 106. Note that for some materials multiple measurements are made and the results iterated until the results agree. After the results agree, the system determines the composition and thickness of layer being measured 106.

Determining Composition and Thickness of SiGe

Figure 2:
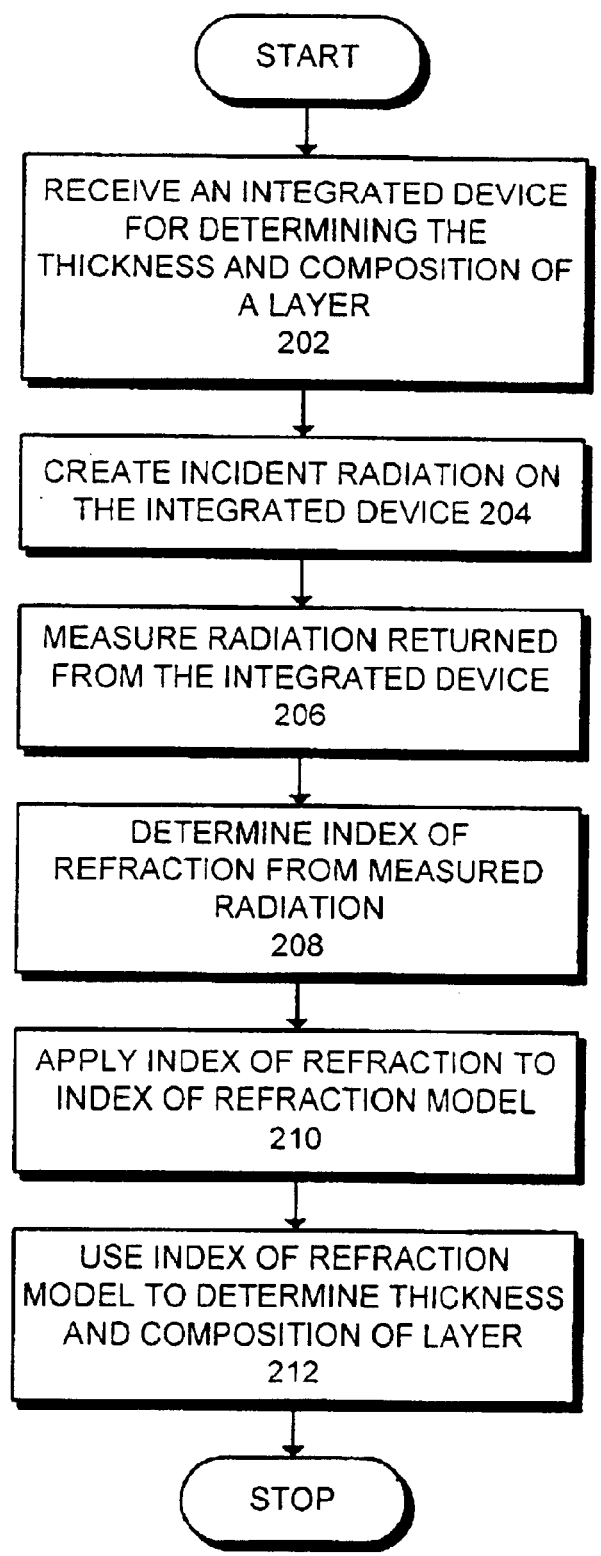
FIG. 2 presents a flowchart illustrating the process of determining the composition and thickness of a layer in accordance with an embodiment of the present invention.

FIG. 2 presents a flowchart illustrating the process of determining the composition and thickness of a layer in accordance with an embodiment of the present invention. The system starts when an integrated device is received (step 202). Next, the layer on the integrated device is exposed to incident radiation (step 204). The system then detects the returned radiation from the integrated device (step 206). The returned radiation includes changes in amplitude, phase, and polarization relative to the incident radiation.

The system then determines the index of refraction from the changes in amplitude, phase, and polarization (step 208). The index of refraction is then applied to an index of refraction model (step 210). Finally, the index of refraction model is used to determine the thickness and the composition of the layer (step 212). Note that this method works well for compositions that are well characterized, such as silicon-germanium (SiGe).

Determining Composition and Thickness of SiGeC

Figure 3:
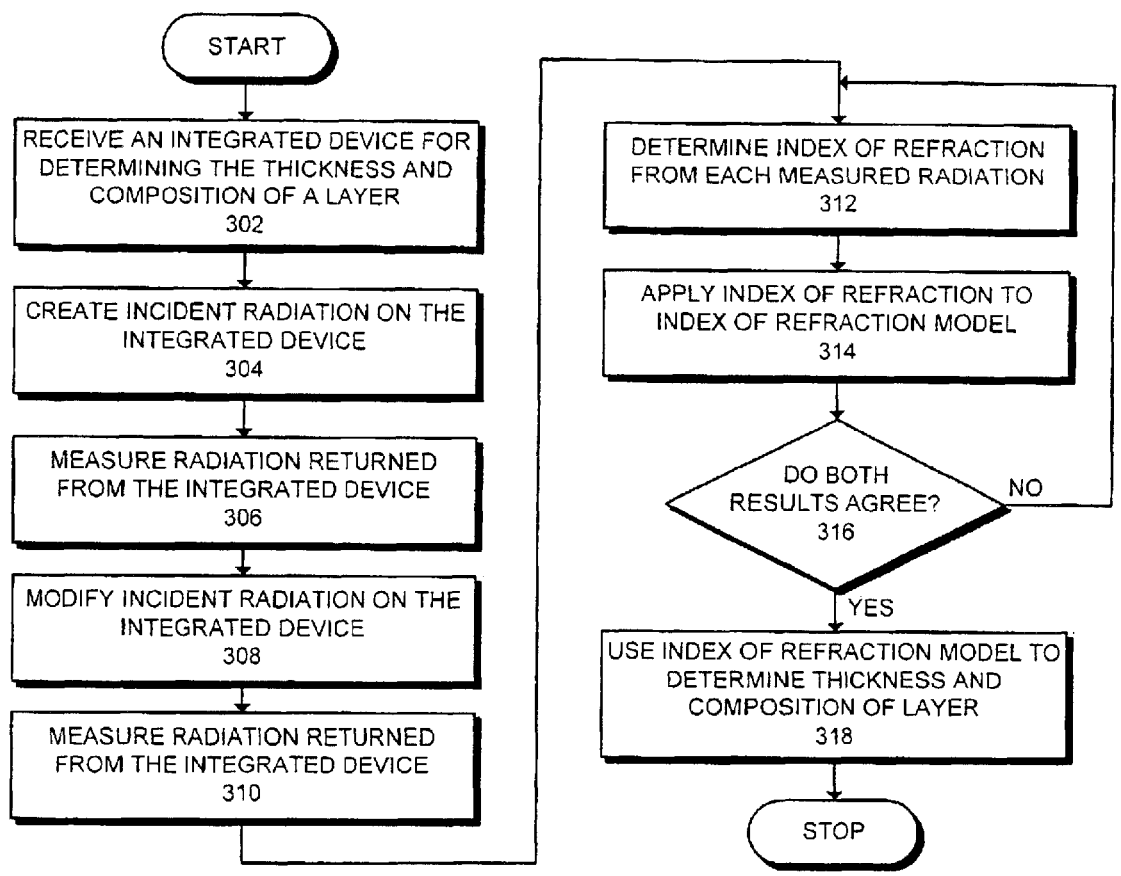
FIG. 3 presents a flowchart illustrating the process of determining the composition and thickness of a layer in accordance with an embodiment of the present invention.

FIG. 3 presents a flowchart illustrating the process of determining the composition and thickness of a layer in accordance with an embodiment of the present invention. The system starts when an integrated device is received (step 302). Next, the layer on the integrated device is exposed to incident radiation (step 304). The system then detects the returned radiation from the integrated device (step 306). The returned radiation includes changes in amplitude, phase, and polarization relative to the incident radiation.

After measuring the changes in amplitude, phase, and polarization from the incident radiation, the system modifies the incident radiation on the integrated device (step 308). This modification can include a change in the wavelength(s) used, a change in the angle of incidence of the wavelength, or other changes. The system then detects the returned radiation from the integrated device (step 310). This operation is similar to the operation in step 306.

The system then determines the index of refraction from each set of measured parameters associated with the returned radiation (step 312). Next, the system applies each of these index of refraction measurements to an index of refraction model (step 314). The system then compares the results from each index of refraction to see if they are equal (step 316). If not, the process returns to step 312 to iterate the solution for the index of refraction. Exit from the loop occurs when the models give the same result for two different sets of data (e.g. angle 1 and angle 2; wavelength 1 and wavelength 2; etc.). If the results are equal at step 316, the system uses the index of refraction model to determine the thickness and composition of the layer (step 318). Note that this method works well for compositions that are not well characterized, such as silicon-germanium-carbon (SiGeC).

The foregoing descriptions of embodiments of the present invention have been presented for purposes of illustration and description only. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A method for determining a composition of a layer within an integrated device, comprising:

receiving the integrated device;

measuring properties of the layer using electro-magnetic radiation;

determining an index of refraction for the layer from the measured properties; and solving for the composition of the layer using the index of refraction, wherein solving for the composition of the layer provides the Ge composition in a SiGe layer.

2. The method of claim 1, wherein the properties measured using ellipsometry include properties of returned radiation received during measurement including a signal amplitude, a signal phase, and a signal polarization.

3. The method of claim 1, wherein determining the index of refraction for the layer involves accounting for an overlaying material layer on the integrated device.

4. A method for determining a thickness of a layer within an integrated device, comprising:

receiving the integrated device;

measuring properties of the layer using electro-magnetic radiation;

determining an index of refraction for the layer from the measured properties; and solving for the thickness of the layer using the index of refraction.

5. The method of claim 4, wherein the properties measured using ellipsometty include properties of returned radiation received during measurement including a signal amplitude, a signal phase, and a signal polarization.

6. The method of claim 4, wherein determining the index of refraction for the layer involves accounting for an overlaying material layer on the integrated device.

7. The method of claim, 4, wherein solving for the thickness of the layer produces the thickness of a SiGe layer.

8. A method for determining a composition of a layer within an integrated device, comprising:

receiving the integrated device;

measuring a first set of properties and a second set of properties of the layer using electro-magnetic radiation, wherein the first set of properties and the second set of properties are measured for different types or conditions of incident radiation;

modeling the first set of properties of the layer to determine a first index of refraction for the layer;

modeling the second set of properties of the layer to determine a second index of refraction for the layer;

applying the first index of refraction and the second index of refraction to index of refraction models;

repeating the steps of modeling the first set of properties modeling the second set of properties, and applying the first index of refraction and the second index of refraction to index of refraction models until results of applying the first index of refraction and the second index of refraction to index of refraction models agree; and solving for the composition of the layer using the index of refraction, wherein solving for the composition of the layer provides the Ge composition and the C composition in a SiGeC layer.

9. The method of claim 8, wherein the properties measured using electro-magnetic radiation include properties of returned radiation received during measurement including a signal amplitude, a signal phase, and a signal polarization.

10. The method of claim 8, wherein the different conditions of incident radiation can have at least one of a different wavelength a different angle, and a combination of different wavelength and different angle.

11. A method for determining a thickness of a layer within an integrated device, comprising:

receiving the integrated device;

measuring a first set of properties and a second set of properties of the layer using electro-magnetic radiation, wherein the first set of properties and the second set of properties are measured for different types or conditions of incident radiation;

modeling the first set of properties of the layer to determine a first index of refraction for the layer;

modeling the second set of properties of the layer to determine a second index of refraction for the layer;

applying the first index of refraction and the second index of refraction to index of refraction models;

repeating the steps of modeling the first set of properties, modeling the second set of properties, and applying the first index of refraction and the second index of refraction to index of refraction models until results of applying the first index of refraction and the second index of refraction to index of refraction models agree; and solving for the thickness of the layer using the index of refraction.

12. The method of claim 11, wherein the properties measured using electro-magnetic radiation include a signal amplitude, a signal phase, and a signal polarization, wherein the signal amplitude, the signal phase, and the signal polarization are parameters of returned radiation received during measurement.

13. The method of claim 11, wherein different conditions include one of a different wavelength, a different angle, and a combination of different wavelength and different angle.

14. The method of claim 11, wherein solving for the thickness provides the thickness of a SiGeC layer.

* * * * *

UNITED STATES PATENT AND TRADEMARK OFFICE
CERTIFICATE OF CORRECTION

PATENT NO.    : 6,884,640 B2
DATED         : April 26, 2005
INVENTOR(S)   : Jeffrey J. Peterson et al.

It is certified that error appears in the above-identified patent and that said Letters Patent is hereby corrected as shown below:

Column 5,
Line 23, please delete the word, "ellipsometty" and replace with the word
-- ellipsometry --

Signed and Sealed this

Twenty-eighth Day of June, 2005

JON W. DUDAS
*Director of the United States Patent and Trademark Office*